United States Patent [19]

Gaffney

[11] Patent Number: 4,788,372

[45] Date of Patent: Nov. 29, 1988

[54] METHANE CONVERSION PROCESS

[75] Inventor: Anne M. Gaffney, West Chester, Pa.

[73] Assignee: Atlantic Richfield Company, Los Angeles, Calif.

[21] Appl. No.: 14,406

[22] Filed: Feb. 13, 1987

[51] Int. Cl.[4] .............................................. C07C 2/00
[52] U.S. Cl. .................................... 585/500; 585/654; 585/656; 585/661; 585/833; 585/905; 585/943; 585/658
[58] Field of Search ............... 585/500, 654, 656, 661, 585/833, 905, 943

[56] References Cited

U.S. PATENT DOCUMENTS

| | | | |
|---|---|---|---|
| 4,495,374 | 1/1985 | Jones | 585/943 X |
| 4,544,786 | 10/1985 | Breder | 585/943 X |
| 4,547,611 | 10/1985 | Jones | 585/943 X |
| 4,554,395 | 11/1985 | Jones | 585/656 X |

FOREIGN PATENT DOCUMENTS 0189079 7/1986 European Pat. Off. .

OTHER PUBLICATIONS

Kimble, James B. et al., "Oxidative Coupling of Methane to Higher Hydrocarbon," Amer. Inst. of Chem. Engrs. meeting in New Orleans, Apr. 6–10, 1986.

Primary Examiner—William R. Dixon, Jr.
Assistant Examiner—James M. Hunter, Jr.
Attorney, Agent, or Firm—William C. Long

[57] ABSTRACT

In a method for converting methane into higher hydrocarbon products and coproduct water which comprises contacting a gas comprising methane and a contact solid comprising at least one reducible metal oxide in the substantial absence of added gaseous oxidant, the improvement comprising conducting at least a portion of the contacting in the presence of added water.

13 Claims, 1 Drawing Sheet

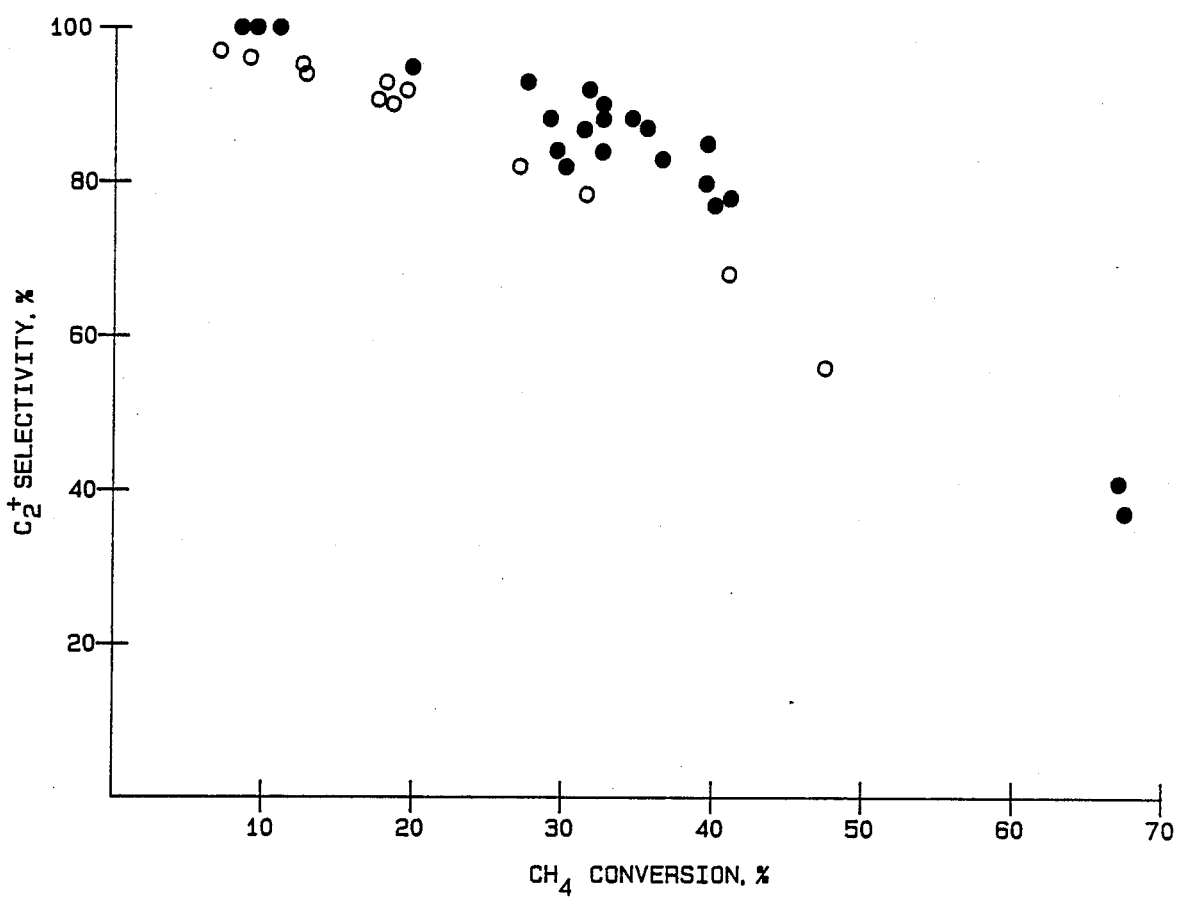

METHANE CONVERSION PROCESS

BACKGROUND OF THE INVENTION

This invention relates to the conversion of methane to higher hydrocarbons. A particular application of this invention is a method for converting natural gas to more readily transportable material.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). Oxidative synthesizing agents are compositions having as a principal component at least one oxide of at least one metal which compositions produce $C_2+$ hydrocarbon products, co-product water, and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony, bismuth, praseodymium, terbium, cerium, iron and ruthenium are most useful. See commonly-assigned U.S. Pat. Nos. 4,443,649 (Mn); 4,444,984 (Sn); 4,445,648 (In); 4,443,645 (Ge); 4,443,674 (Pb); 4,443,646 (Bi); 4,499,323 (Pr); 4,499,324 (Ce); and 4,593,139 (Ru), the entire contents of which are incorporated herein by reference. See also commonly-assigned U.S. patent application Ser. No. 06/666,694 (Fe) the entire content of which is incorporated herein by reference.

Commonly-assigned U.S. Pat. No. 4,554,395 discloses and claims a process which comprises contacting methane with an oxidative synthesizing agent under elevated pressure (2–100 atmospheres) to produce greater amounts of $C_3+$ hydrocarbon products.

Commonly-assigned U.S. Pat. No. 4,560,821 discloses and claims a process for the conversion of methane to higher hydrocarbons which comprises contacting methane with particles comprising an oxidative synthesizing agent which particles recirculate between two physically separate zones—a methane contact zone and an oxygen contact zone.

The reaction products of such processes are hydrocarbons, carbon oxides, coke and water. It would be beneficial in these processes to reduce selectivities to carbon oxides and coke and to increase methane conversions to the desired hydrocarbon products. Accordingly, an object of this invention is to provide an improved process for converting methane to higher hydrocarbons. More particular aspects, objects and the several advantages of this invention will become apparent to those skilled in the art upon reading this disclosure and the appended claims.

SUMMARY OF THE INVENTION

It has now been found that processes for producing higher hydrocarbons wherein methane is contacted in the substantial absence of added gaseous oxidant with a solid comprising at least one reducible metal oxide are improved when the contacting is conducted in the presence of added water. This added water is separate and apart from the coproduct water produced from methane conversion during the contacting. However, such coproduct water (or a portion thereof) may be separated from the other products and introduced into the contacting zone as the added water.

In processes conducted according to the method of this invention, methane is converted to higher hydrocarbons with improved efficiency, e.g., increased selectivity to higher hydrocarbon products.

BRIEF DESCRIPTION OF THE DRAWING

The FIGURE is a plot of $C_2+$ hydrocarbon product selectivity vs. methane conversion for the tests described in Example 13.

DETAILED DESCRIPTION OF THE INVENTION

In addition to methane the methane feedstock employed in the method of this invention may contain other hydrocarbon or non-hydrocarbon components. The methane content of the hydrocarbon portion of the feedstock, however, will typically be within the range of about 40 to 100 vol. %, preferably within the range of about 80 to 100 vol. %, more preferably within the range of about 90 to 100 vol. %.

The amount of added water present during at least a portion of the methane/contact solid contacting may vary over a wide range. Preferably, the mole ratio of added water to methane in the gas to be contacted is less than 10. More preferably, this mole ratio is in the range of about 0.01 to 6, still more preferably about 0.05 to about 4. The added water may be combined with the gas feed prior to the contacting. For example, the gaseous feed comprising methane may be contacted with water so that the gas "picks-up" a predetermined, controlled amount of added water prior to contacting the solid catalyst. Alternately, a predetermined, controlled amount of water, e.g., steam, can be injected into the methane-containing gas and/or directly into the contacting zone.

While solids employed in the method of this invention are sometimes referred to as a "catalyst", it will be understood that, under conditions of use, it serves as a selective oxidant, and, therefore, takes on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, the catalysts comprise at lease one reducible oxides of at least one metal, which oxide when contacted with methane at synthesizing conditions (e.g., at a temperature within the range of about 500° to 1000° C.) produces higher hydrocarbon products, coproduct water, and a reduced metal oxide. The term "reducible" is used to identify those oxides of metals which are reduced under the aforesaid conditions. The term "reducible oxides of metals" includes (1) compounds described by the general formula $M_xO_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components for methane conversion.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (Pr) and also see commonly-assigned U.S. patent application Serial No. 06/600,918 (Tb).

Reducible oxides of iron and ruthenium are also effective, particularly when associated with an alkali or alkaline earth component. See commonly-assigned U.S. patent application No. 06/600,730 (Fe) and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorus into solids promoted by alkali or alkaline earth components enhances catalyst stability. See commonly-assigned U.S. Pat. Nos. 4,499,322 and 4,495,374, the entire contents of which are incorporated herein by reference. Alkali metals are selected from the group consisting of lithium, sodium, potassium, rubidium and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compostions derived from magnesia have been found to be particularly effective catalytic materials.

Boron and compounds thereof are also desirably present in the catalyst employed in the process of this invention. See commonly-assigned U.S. patent application Ser. No. 06/877,574, entire content of which is incorporated herein by reference. One class of boron-promoted compositions useful in the process of this invention comprises:

(1) at least one reducible metal oxide,
(2) at least one member of the group consisting of boron and compounds thereof, and
(3) at least one member of the group consisting of oxides of alkaline earth metals.

A related class of catalyst compositions further comprises at lease one alkali metal or compound thereof. Sodium and lithium are preferred alkali metal components.

One further, special class of catalyst compositions useful in the process of this invention are mixed oxides of sodium, magnesium, manganese and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of Mn relative to at lease one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted, reducible metal oxides are disclosed in U.S. Pat. No. 4,544,784. Methane conversion processes employing chalcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred. of the methods associated with similar compositions known in the art. Thus, such methods as precipitation, coprecipitation, impregnating, granulation, spray drying or dry-mixing can be used. Supported solids may be prepared by methods such as adsorption, impregnation, precipitation, co-precipitation, and dry-mixing. For example, compounds of Mn,Sn,In,Ge,Pb,Sb,Bi,Pr,Tb,Ce,Fe and or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodies. After impregnation the preparation is dried to remove solvent and the dried solid is calcined at a temperature selected within the range of about 300° to 1200° C. Particular calcination temperatures will vary depending on the compounds employed. Preferably, the alakline earth component is provided as the oxide. Preferably, the alkali metal component is provided as a basic composition of the alkali metal(s). Examples are The catalysts are conveniently prepared by any of the methods associated with similar compositions known in the art. Thus, such methods as precipitation, coprecipitation, impregnating, granulation, spray drying or dry-mixing can be used. Supported solids may be prepared by methods such as adsorption, impregnation, precipitation, co-precipitation, and dry-mixing. For example, compounds of Mn,Sn,In,Ge,Pb,Sb,Bi,Pr,Tb,Ce,Fe and or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4)

an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodies. After impregnation the preparation is dried to remove solvent and the dried solid is calcined at a temperature selected within the range of about 300° to 1200° C. Particular calcination temperatures will vary depending on the compounds employed. Preferably, the alakline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of the crystalline compound, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, $H_2$, carbon oxides, steam, and/or inert gases such as $N_2$ and the noble gases.

Preferably, methane is contacted with reducible metal oxides in the presence of added water and in the substantial absence of catalytically effective nickel, noble metals and compounds thereof, (i.e., nickel, rhodium, palladium, silver, osmium, iridium, platinum and gold) to minimize the deleterious catalytic effects thereof. These metals, when contacted with methane at the temperatures employed in the methane contacting step of the present invention, tend to promote coke formation, and the metal oxides tend to promote the formation of combustion products rather than the desired hydrocarbons. The term "catalytically effective" is used herein to identify the quantity of one or more of nickel and the noble metals and compounds thereof which substantially changes the distribution of products obtained in the method of this invention relative to such contacting in the absence of such metals and compounds thereof.

Operating temperatures for the methane contacting step are generally within the range of about 500 degrees to 1000 degrees C. Best results for contact solids containing manganese have been found at operating temperatures within the range of about 800 degrees to 900 degrees C. Reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850 degrees C.); (2) reducible oxides of germanium (operating temperatures will preferably not exceed about 850 degrees C.); and (3) reducible oxides of bismuth (operating temperatures will preferably not exceed about 850 degrees C.).

Operating pressures for the methane contacting step are not critical to the presently claimed invention. However, both general system pressure and partial pressures of methane and water have been found to effect overall results. Preferred general system pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 100 to 300,000 hr.$^{-1}$, more preferably within the range of about 600 to 100,000 hr.$^{-1}$.

Contacting methane and a reducible metal oxide to form higher hydrocarbons also produces coproduct water and reduces the metal oxide. The exact nature of the reduced metal oxides are unknown, and so are referred to as "reduced metal oxides". Regeneration of reducible metal oxides is readily accomplished by contacting the reduced composition with oxygen (e.g., an oxygen-containing gas such as air) for a period of time sufficient to produce a reducible metal oxide from at least a portion of the reduced composition. Oxygen contacting temperatures are preferably within the range of about 300 degrees C. to 1200 degrees C., more preferably within the range of about 500 degrees C. to 1000 degrees C.

A single reactor apparatus containing a fixed bed of contact solids, for example, may be used with intermittent or pulsed flow of a first gas comprising methane and added water and a second gas comprising oxygen (e.g., oxygen, oxygen diluted with an inert gas, or air, preferably air), which may also contain added water.

In another embodiment, the methane contacting step and the oxygen contacting step are performed in physically separate zones with contact solids recirculating between the two zones. Thus, a suitable method for synthesizing hydrocarbons from a methane source comprises: (a) contacting a gas comprising methane and added water and particles comprising a reducible metal oxide to form higher hydrocarbon products, coproduct water, and particles comprising a reduced metal oxide; (b) removing particles comprising a reduced metal oxide from step (a) and contacting the reduced solids with an oxygen-containing gas which may also contain added water to form particles comprising a reducible metal oxide; and (c) returning particles comprising a reducible metal oxide formed in step (b) to step (a). Steps (a), (b) and (c) are preferably repeated at least periodically, and more preferably the steps are continuous. Thus, in this more preferred embodiment, solids are continuously circulated between at least one methane, water-contact zone and at least one oxygen-contact zone, the latter optionally also having water added thereto.

Gas/solid contacting steps may be performed according to any of the known techniques: e.g., the solids may be maintained as fixed beds, fluidized beds, moving beds, ebullating beds, etc.

The effluent from the methane contact zone contains higher hydrocarbon products (e.g., ethylene, ethane and other lighter hydrocarbons), carbon oxides, water and unreacted hydrocarbon (e.g., methane). Higher hydrocarbons may be recovered from the effluent and, if desired, subjected to further processing using techniques known to those skilled in the art. Unreacted methane may be recovered and recycled to the contact zone.

The invention is further illustrated by reference to the following examples.

EXAMPLE 1

Solid particles of MgO (supplied by Kaiser Chemical) and appropriate amounts of boron (as boric acid), lithium (as lithium hydroxide), and manganese (as manganese dioxide) were mixed to form an aqueous slurry, and the slurry was ball-milled for 2-3 hours. The milled slurry was spray dried and then calcined at 900° C. for 4-5 hours. The components of calcined solids were present in the following atomic ratio: 0.5 B: 0.5 Li: 1 Mn: 2.5 Mg.

EXAMPLES 2-3 and COMPARATIVE EXAMPLES A-B

A portion (12.6 grams) of solids produced and described in Example 1 (the solids having a particle size of 12-28 mesh) was placed in a tubular alumina, fixed bed reactor. The reactor was brought up to reactor temperature under a flow of heated air before introducing methane feed. When steam was used, the steam was continuously introduced and the reactor system was operated according to the following methane, $N_2$ and air cycle: methane feed/$N_2$ purge/air regeneration/$N_2$ purge. The same methane/$N_2$/air cycle was followed when no steam was added. Cumulative samples of effluent were collected during the methane contact portion of the cycle and the samples were analyzed. Also the air regeneration effluent is collected for coke analysis. Results obtained are described in Table 1. The results include methane contact runs performed with and without added steam. All methane contact runs reported in Table 1 were prepared at 840° C. and a methane gas hourly space velocity (GHSV) of 2400 hr.$^{-1}$.

TABLE I

| Example | Methane Run Length (Sec.) | % $CH_4$ Conv. | % $C_2+$ Selectivity | Mole % Steam in $CH_4$ Feed |
| --- | --- | --- | --- | --- |
| 2 | 30 | 20 | 88 | 20 |
| A | 30 | 22 | 80 | 0 |
| 3 | 60 | 17 | 91 | 20 |
| B | 60 | 21 | 84 | 0 |

EXAMPLE 4

Solid particles of MgO (supplied by Kaiser Chemical) and appropriate amounts of boron (as boric acid), sodium (as sodium hydroxide), and manganese (as manganese dioxide) were mixed to form an aqueous slurry, and the slurry was ball-milled for 2-3 hours. The milled slurry was spray dried and then calcined at 950° C. for 4-5 hours. The components of the calcined solids were present in the following atomic ratio: 0.5 B: 1 Na: 1 Mn: 2.5 Mg.

EXAMPLES 5-12 and COMPARATIVE EXAMPLES C-F

A portion (10.9 grams) of the solids produced as described in Example 4 (the solids having a particle size of 12-28 mesh) was placed in tubular, alumina, fixed bed reactor. The reactor was brought up to reaction temperature under a flow of heated air before introducing methane feed. The reactor system was operated according to the cycle as described above for Examples 2-3 and Comparative Examples A-B. Results obtained are described in Table II. All methane contact runs reported in Table II were performed at a methane GHSV of 2400 hr.$^{-1}$.

TABLE II

| Example | Methane Run Length (Sec.) | Temp. (°C.) | % $CH_4$ Conversion | % $C_2+$ Selectivity | Mole % Steam in $CH_4$ Feed |
| --- | --- | --- | --- | --- | --- |
| 5 | 15 | 800 | 16 | 73 | 20 |
| C | 15 | 800 | 10 | 72 | 0 |
| 6 | 30 | 800 | 15 | 74 | 20 |
| D | 30 | 800 | 11 | 72 | 0 |
| 7 | 15 | 825 | 21 | 70 | 20 |
| E | 15 | 825 | 21 | 63 | 0 |
| 8 | 30 | 825 | 18 | 72 | 20 |
| F | 30 | 825 | 18 | 66 | 0 |
| 9 | 15 | 840 | 25 | 67 | 20 |
| 10 | 30 | 840 | 22 | 70 | 20 |
| 11 | 15 | 860 | 29 | 64 | 20 |
| 12 | 30 | 860 | 26 | 68 | 20 |

EXAMPLE 13

Solid particles of MgO (supplied by Kaiser Chemical) and appropriate amounts of boron (as boric acid), lithium (as lithium hydroxide), manganese (as manganese dioxide), and silica were mixed to form an aqueous slurry, and the slurry was ball-milled for 2-3 hours. The milled slurry was spray dried and the pelletized cyclone material was calcined at 1000° C. for 4-5 hours. The components of the calcined solids were present in the following atomic ratio:

0.6 B: 0.5 Li: 1 Mn: 2.9 Mg: 0.3Si

A portion of the these solids was placed in a tubular, alumina, fixed bed reactor. The reactor was brought up to reaction temperature under a flow of heated air before introducing methane feed. The reactor system was operated according to the cycle as described above for Examples 2-3 and Comparative Examples A-B. Reaction temperatures ranged from 800°-850° C., methane WHSV ranged from 0.5-2 hr.$^{-1}$, methane run length ranged from 15 sec. to 1 minute. Where steam was employed, the mole ratio of steam/methane was 3/1.

The results obtained both with and without the addition of steam are graphically presented in the accompanying FIGURE which is a plot of $C_2$ +selectivity versus methane conversion.

An examination of the plotted results clearly evidences the fact the addition of steam has an important effect on reaction selectivity for a particular methane conversion. Significantly improved selectivities to the desired $C_2$ +hydrocarbons are obtained through the use of steam as compared to run in which no steam was added to the feed.

What is claimed:

1. In a method for converting methane into higher hydrocarbon products and coproduct water which comprises contacting a gas comprising methane with a solid comprising at least one reducible metal oxide of a least one metal, which oxide when contacted with methane at 500° to 1000° C. produces higher hydrocarbons, coproduct water, and reduced metal oxide, in the substantial absence of added gaseous oxidant, the improvement comprising conducting at least a portion of said contacting in the presence of added water.

2. The method of claim 1 wherein the mole ratio of said added water to said methane in said gas is less than about 10.

3. The method of claim 1 wherein the mole ratio of said added water to methane is in the range of about 0.01 to about 6.

4. The method of claim 1 wherein the mole ratio of said added water to said methane in said gas is in the range of about 0.05 to about 4.

5. The method of claim 1 wherein said added water is combined with said gas prior to said contacting.

6. The method of claim 1 wherein said added water is present during at least the initial part of said contacting.

7. The method of claim 1 wherein said contacting occurs at a temperature in the range of about 500° C. to about 1000° C.

8. The method of claim 1 wherein said contacting occurs at a temperature in the range of about 800° C. to about 900° C.

9. The method of claim 1 wherein the solid comprises at least one reducible oxide of Mn, Sn, In, Ge, Pb, Sb, Bi, Pr, Tb, Ce, Re and Ru.

10. The method of claim 1 wherein the solid comprises at least one reducible oxide of Mn.

11. The method of claim 9 wherein the solid comprises at least one reducible oxide of Mn, Sn, In, Ge, Pb, Bi, Pr, Tb, Ce, Re, and Ru and also comprises at least one member of the group consisiting of alkali metals, alkaline earth metals, and compounds and mixtures thereof.

12. The method of claim 9 wherein the solid comprises at least one reducible oxide of Mn, Sn, In, Ge, Pb, Bi, Pr, Tb, Ce, Re, and Ru and also comprises at least one member of the group consisting of boron and compounds thereof.

13. The method of claim 10 wherein the solid comprises at least one reducible oxide of Mn and also comprises at least one member of the group consisting of boron and compounds thereof.

* * * * *